US012690622B2

(12) United States Patent
Lakraa et al.

(10) Patent No.: US 12,690,622 B2
(45) Date of Patent: Jul. 28, 2026

(54) ELECTRONIC CIGARETTE WITH A SENSOR INTEGRATED INTO A DISPLAY UNIT

(71) Applicant: JT International SA, Geneva (CH)

(72) Inventors: Karima Lakraa, Lausanne (CH); Joao Seco, Geneva (CH)

(73) Assignee: JT International SA, Geneva (CH)

( * ) Notice: Subject to any disclaimer, the term of this patent is extended or adjusted under 35 U.S.C. 154(b) by 369 days.

(21) Appl. No.: 17/774,738

(22) PCT Filed: Nov. 2, 2020

(86) PCT No.: PCT/EP2020/080649
§ 371 (c)(1),
(2) Date: May 5, 2022

(87) PCT Pub. No.: WO2021/089465
PCT Pub. Date: May 14, 2021

(65) Prior Publication Data
US 2022/0386702 A1      Dec. 8, 2022

(30) Foreign Application Priority Data

Nov. 6, 2019    (EP) ..................................... 19207533

(51) Int. Cl.
*A24F 40/51*          (2020.01)
*A24F 40/10*          (2020.01)
(Continued)

(52) U.S. Cl.
CPC .............. *A24F 40/51* (2020.01); *A24F 40/40* (2020.01); *A24F 40/60* (2020.01); *A61B 5/02438* (2013.01); *G06V 40/13* (2022.01)

(58) Field of Classification Search
None
See application file for complete search history.

(56) References Cited

U.S. PATENT DOCUMENTS

2011/0267298 A1* 11/2011 Erhart ..................... G06F 21/32
                                                    345/173
2013/0104916 A1*  5/2013 Bellinger .............. A61M 15/06
                                                    131/328
(Continued)

FOREIGN PATENT DOCUMENTS

CN        105125222 A      12/2015
CN        207075558 U  *  3/2018
(Continued)

OTHER PUBLICATIONS

CN207075558U ENglish Translation obtained from Espacenet, pp. 1-15 (Year: 2018).*
(Continued)

*Primary Examiner* — Philip Y Louie
*Assistant Examiner* — Madeleine P Delacruz
(74) *Attorney, Agent, or Firm* — Lerner David LLP

(57)          ABSTRACT
An electronic cigarette includes an external housing and display unit configured to receive user input and display operational status of the electronic cigarette. The external housing includes an aperture for receiving the display unit. A sensor is integrated into the display unit to detect user characteristics. A controller of the electronic cigarette is configured to retrieve information from the sensor and control the operation of the electronic cigarette.

15 Claims, 6 Drawing Sheets

(51) Int. Cl.

| | |
|---|---|
| *A24F 40/40* | (2020.01) |
| *A24F 40/49* | (2020.01) |
| *A24F 40/53* | (2020.01) |
| *A24F 40/60* | (2020.01) |
| *A24F 40/70* | (2020.01) |
| *A61B 5/024* | (2006.01) |
| *G06V 40/13* | (2022.01) |

(56) References Cited

U.S. PATENT DOCUMENTS

| | | | | |
|---|---|---|---|---|
| 2015/0122252 A1* | 5/2015 | Frija | A24F 40/65 | |
| | | | 128/202.21 | |
| 2016/0029697 A1 | 2/2016 | Shafer | | |
| 2017/0181471 A1* | 6/2017 | Phillips | A24F 40/70 | |
| 2018/0160734 A1* | 6/2018 | Batista | G06V 40/1365 | |
| 2018/0338527 A1* | 11/2018 | Sur | A61B 5/33 | |
| 2020/0138111 A1* | 5/2020 | Angelico | A24F 40/53 | |
| 2020/0315254 A1* | 10/2020 | Zielazek | A24F 40/60 | |
| 2022/0053836 A1* | 2/2022 | Cazzoli | A61M 15/06 | |

FOREIGN PATENT DOCUMENTS

| | | | | | |
|---|---|---|---|---|---|
| CN | 207519630 | U | 6/2018 | | |
| EP | 3711582 | A1 | 9/2020 | | |
| WO | 15018479 | A1 | 2/2015 | | |
| WO | 2015174708 | A1 | 11/2015 | | |
| WO | WO-2016009202 | A1 * | 1/2016 | ............ | A24F 15/18 |
| WO | 2019122874 | A1 | 6/2019 | | |
| WO | 2019175810 | A1 | 9/2019 | | |

OTHER PUBLICATIONS

International Search Report for Application No. PCT/EP2020/080649 mailed Apr. 12, 2021, pp. 1-6.

Search Report dated Mar. 21, 2025 from the Office Action for Chinese Application No. 202080076423.5 issued Mar. 28, 2025. 3 pages.

Search Report dated Aug. 26, 2025 from the Office Action for Chinese Application No. 202080076423.5 issued Aug. 29, 2025, 2 pages.

* cited by examiner

ELECTRONIC CIGARETTE WITH A SENSOR INTEGRATED INTO A DISPLAY UNIT

CROSS-REFERENCE TO RELATED APPLICATIONS

The present application is a national phase entry under 35 U.S.C. § 371 of International Application No. PCT/EP2020/080649, filed Nov. 2, 2020, published in English, which claims priority to European Application No. 19207533.1 filed Nov. 6, 2019, the disclosures of which are incorporated herein by reference.

FIELD OF INVENTION

The present invention relates to an electronic cigarette, and the manufacture thereof.

BACKGROUND

Electronic cigarettes typically have a housing to accommodate working components, including a battery and electronic control circuitry (e.g. printed circuit board, puff sensors, switches). Such housings are generally elongate in shape for a user to hold, similar to conventional cigarettes, and can be made by extruding a material (plastic or metallic) through a die. The working components are generally provided on a drawer insert which is then introduced into the housing from one of its ends. An example of such an assembly is disclosed in WO15018479. It has been found that this configuration can cause damage to the electronic working components during insertion which may lead to less reliable products.

In view of the above-mentioned drawbacks, it is an object of the invention is to provide a more reliable electronic cigarette.

SUMMARY

According to the present invention there is provided an electronic cigarette, comprising: an external housing; a sensor configured to detect a characteristic from the user; a display unit located in an aperture of the external housing and configured to receive user input and display operational status of the device, wherein the sensor is integrated into the display unit.

In this way the sensor is combined with a display in the display unit to provide a device that is simpler to use as well as allowing increased functionality to be provided to a user within the limited real estate of an electronic cigarette. The sensors may be biometric sensors that gather information from a user in order to improve user experience of the electronic device. By providing sensors in the display unit, the electronic cigarette of the present invention will also be more intuitive for a user to operate.

Preferably the display comprises a plurality of layers, where a first layer is configured to sense an input from the user and activate the sensor. In this way a first sensing layer, which is preferably a touch-screen layer, provides an activation function to the sensor before the sensor can be used to detect user characteristics. The sensing layer may have the same area as the display or have a smaller area, thereby providing the input sensing to a limited zone.

Preferably the electronic cigarette further comprises a second layer which is an input area of the sensor. In this way the sensor is provided as a second layer in the display unit where, following activation, a user characteristic can be detected within the input area of the sensor. By use of known conductive layering techniques the second sensing layer may also be integrated within the area of the display, or may have a smaller area than the display, thereby providing a user characteristic detection zone. Using limited zones to provide different functions (e.g. activation, biometric detection) simplifies the manufacture of a display unit. Each zone may preferably also respond to different commands, for example, an activation zone may require a swiping gesture and a user characteristic detection zone may require a pressing motion for a predetermined time period.

Preferably the second layer is activated based on activation of the first layer. In this way user characteristics are only measured following a discrete activation command. This prevents undesired readings, for example from another person, to be mistakenly detected. Advantageously the activation function provides a lock function to display unit of the electronic cigarette Preferably the first layer and the second layer are superposed. In this way multiple layers can be provided on top of each other in an overlapping manner.

Preferably the second layer is a pixeled layer and wherein the first layer defines the reading zone of the pixeled second layer. In this way the pixeled layer can be used as a sensing layer where the first layer is configured to indicate where the reading zone of the second layer, or sensing region, is positioned in the display unit of the electronic cigarette. In other words information from the first layer is sent to the controller which then defines the reading zone of the second layer.

Preferably the sensor is configured to detect a movement or position in space of the electronic cigarette. In this way the sensor can detect user motion and display operational information when it detects that the electronic cigarette is being used according to a pre-set manner. For example the sensor can be an accelerometer.

Preferably the electronic cigarette according to any one of the preceding claims, wherein the sensor is a biometric sensor. In this way the sensor can detect biometric information of a user, such as pulse/heart-rate, blood oxygen levels and/or user temperature. This information may be used to activate the electronic cigarette device and/or display the information to the user.

The sensor may be an optical sensor. In this way the sensor can detect light to activate and/or operate the display unit. The sensor may be a fingerprint reader. In this way the sensor can detect fingerprint biometrics to activate the device. Other biometric sensing functions may also be provided via a fingerprint reader, such as pulse or blood-oxygen monitoring. The sensor may preferably be provided as a sensing layer comprising an array of finger biometric pixels. The sensor may be a heart rate sensor.

Preferably the electronic cigarette comprises an additional sensor located on the external housing of the electronic cigarette. In this way multiple sensors can be incorporated into the electronic cigarette, where the additional sensor is configured to communicate with the display unit. The additional sensor is preferably located within a notch or depression on an opposite or opposing surface to the outer surface of the display unit. This allows a user to operate both the display unit and the additional sensor with one hand, for example by gripping the electronic cigarette between a finger and a thumb. Preferably the external housing comprises an electrically conductive material and is connected to a circuit registering a heartbeat.

Preferably the electronic cigarette according further comprises a controller configured to retrieve information from the sensor and control the operation of the device. In this way the controller can operate the electronic cigarette based on information received from the sensor. For instance, there can be a plurality of users associated with the device and the e-cig can calibrate the device (vapor volume, allowable timings and nicotine intake etc.) after detecting the specific user or person using the device. The controller may preferably provide a lock mechanism to the electronic cigarette which must be de-activated before the e-cig can be used. Of course, one major advantage of the fingerprint authorization for example is to avoid child or underage use of the device.

Preferably the display unit is provided as an exterior surface, such as a top surface on an insert, comprising at least one electronic component. In this way the display unit can be placed into the external housing in a mounted arrangement. By using a mounted arrangement the manufacturing process is simplified, thereby reducing the risk of damage during production.

In the present disclosure there is provided an electronic cigarette, comprising: an insert comprising at least one electronic component; a housing sleeve comprising a body with a first end and a second end, wherein the housing sleeve comprises an opening along a length of the body between the first end and the second end, and wherein the opening is arranged to receive the insert within the housing sleeve.

In this way the opening allows electronic components to be placed into a housing sleeve in a mounted arrangement. This minimises the risk of damaging electronic components which are introduced into the housing sleeve, as compared to inserting electronic components via an end of a sleeve in a sliding manner where the components may be damaged as they are pushed into position. Providing an opening along the length of the housing sleeve allows aerosol generation devices to be easily and reliably manufactured, reworked or repaired in a cost-effective way. For example a battery can be easily replaced, or access to a printed circuit board, PCB, for reworking is improved by providing access along the length of the housing sleeve.

Preferably the insert further comprises a lid sized and shaped to match the opening. In this way the lid reliably closes the opening and provides protection to the at least one electronic component. The lid may have a rim having a geometry configured to engage with the circumferential edge of the opening in the housing. The outer surface of the lid may be flush with the outer surface of the housing sleeve, or be textured (to provide additional grip) according to design requirements. Alternatively the outer surface of the lid may not be flush in order to include further features (e.g. magnetic or mechanical push-fit connections) which interact with other components, such as a stand or case for the electronic cigarette.

Preferably the lid comprises a display. In this way the lid provides additional display functionality to the aerosol generation device. For example the display may indicate the battery power level of the device, or user information such as puff count or duration of use. The electronic cigarette may also be wirelessly connected to a third party device, such as a smartphone, and provide notifications from the third party device.

The at least one electronic component may comprise one or more of: a battery, a printed circuit board, PCB, and a sensor. In this way different electronic components can be introduced into a housing sleeve via the insert.

The at least one electronic component may be an airflow sensor. In this way the insert can be configured to further interact with a capsule or pod to calculate the amount of aerosol inhaled by a user. The insert may further comprise a housing for the airflow sensor, the housing being configured to receive a portion of the airflow sensor and provide a reduced pressure space.

Preferably the lid comprises a material of higher flexibility than the housing sleeve. In this way the lid and/or display can clip or snap onto the housing via a push-fit connection. For example the lid material may be made of plastic such as polymethyl methacrylate, glass or a combination thereof.

Preferably the display has a connection rim, preferably in metal. The connection rim may be configured to receive a fastener configured to attach the metallic connection rim to the circumferential edge or rim of the housing.

Preferably the insert comprises a wireless antenna positioned below the lid and that is arranged to communicate data therethrough. In this way the lid can be easily constructed at low cost and is also suitable for display and wireless communication purposes. The aerosol generation device can communicate with a user device via a wireless antenna, and where the lid allows wireless communication to easily pass through.

Preferably the housing sleeve comprises a metallic material. In this way transmission of wireless data occurs preferentially through the lid of the device. Hence, the lid provides a surface that facilitates the transmission of radio waves.

Preferably the housing sleeve has a closed end and an open end. In this way the housing sleeve can be easily constructed, for example by extrusion or injection moulding. The housing sleeve may have a cross-sectional shape which is substantially rhombus shaped, oval, circular, square or rectangular.

Preferably the opening is located at a major surface or at a side of the housing sleeve. In this way the insert can be easily introduced within the housing sleeve and away from the ends of the housing sleeve thereby reducing the risk of damage to the at least one electronic component.

The electronic cigarette may further comprise a closing element at the first end. In this way the closing element, for example a plug, provides a seal at the first end of the aerosol generation device.

Preferably the closing element comprises a port, the port configured to provide electrical or data communication access to the at least one electronic component. In this way the first end can be used as an access point to the at least one electronic component of the mounted insert. The port may be made from a radio transparent material similar to that of the display. The port may also comprise embedded magnets which may be used as connections to further enhance the functionality of the electronic cigarette.

Preferably the electronic cigarette further comprises a cartridge seating or a liquid store at the second end. In this way a cartridge or liquid store may be received in the housing sleeve in order for the electronic components to provide electrical energy to a heating element in the cartridge or take measurements, such as a heating element temperature or aerosol generating liquid volume, from the cartridge.

There is also provided a method of manufacturing the electronic cigarette according any of the preceding claims, comprising: providing an insert comprising at least one electronic component; providing a housing sleeve comprising a body with a first end and a second end, wherein the housing sleeve comprises an opening along a length of the body between the first end and the second end, and wherein the opening is arranged to receive the insert within the housing sleeve; and mounting the insert within the housing sleeve via the opening. In this way electronic components can be placed into a housing sleeve using a mounted arrangement, which simplifies the assembly process and reduces the risk of damage to electronic components.

BRIEF DESCRIPTION OF THE DRAWINGS

Embodiments of the invention are now described, by way of example, with reference to the drawings, in which.

DETAILED DESCRIPTION

Figure 1A:
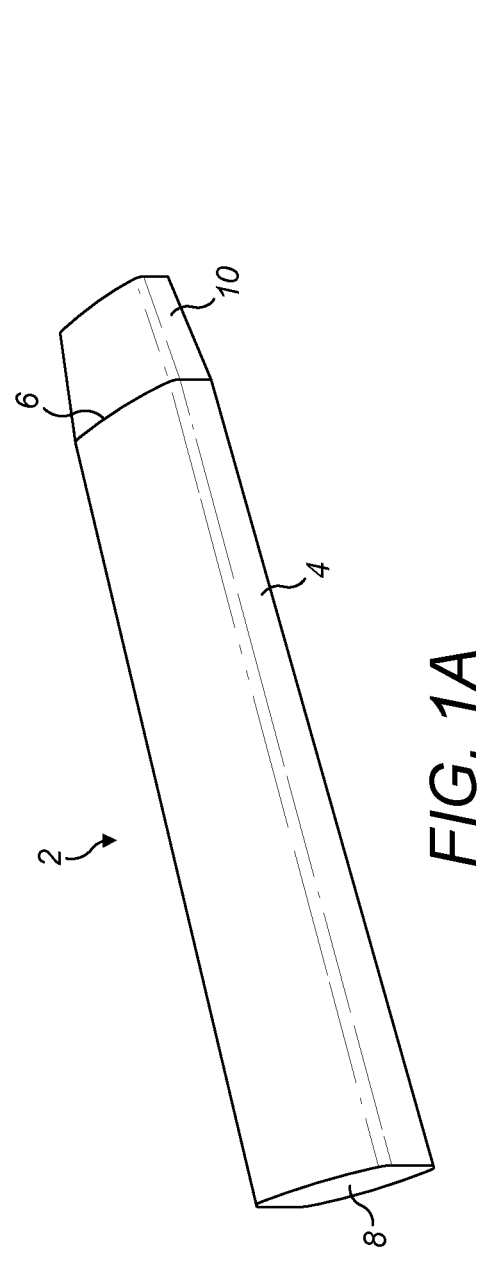
FIG. 1A is perspective view of a known electronic cigarette device in an assembled configuration.
Figure 1B:
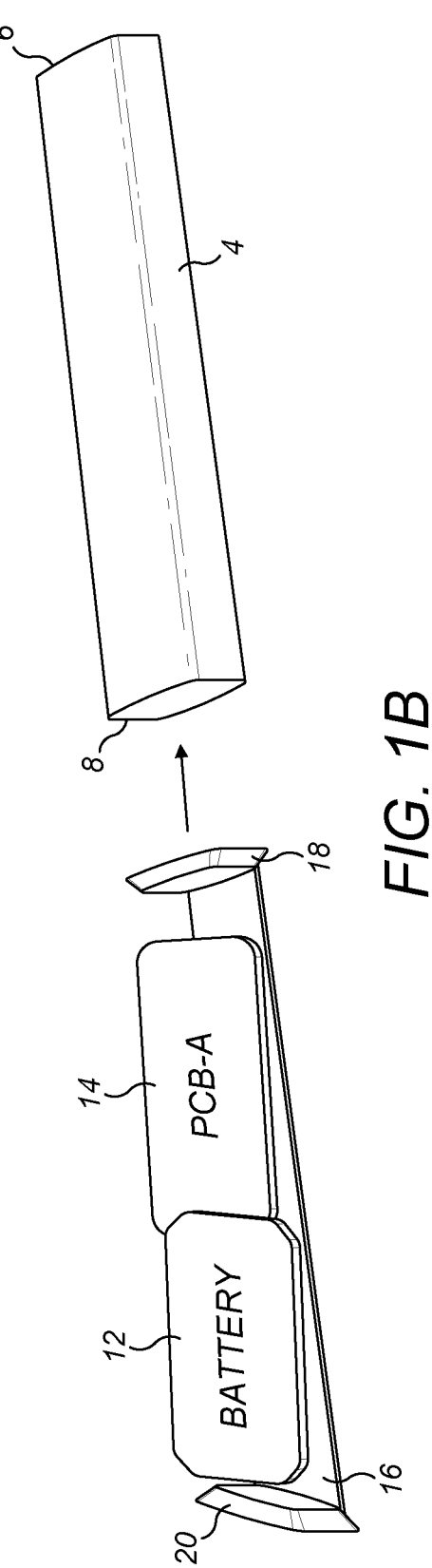
FIG. 1B is a perspective view of a known electronic cigarette device in a pre-assembled configuration.

FIGS. 1A and 1B show an electronic cigarette 2 known from the prior art. The electronic cigarette includes a sleeve 4 with a mouthpiece end 6 and a charging end 8. A capsule, or pod, 10 is provided at the mouthpiece end 6, and electronic components, which include a battery 12 and a printed circuit board 14, are provided on a drawer 16 for insertion via the charging end 8 into the sleeve 4. The drawer 16 has a capsule contact portion 18 and a plug portion 20 arranged such that the capsule contact portion 18 is slidingly inserted into the sleeve 4 through the charging end 8 as shown in FIG. 1B.

The sleeve 4 has a closed end at the charging end 8 and an open end at the mouthpiece end 6 when the drawer 16 is fully inserted into the sleeve 4. In other words, the capsule contact portion 18 does not extend through to the mouthpiece end 6 when the drawer 16 is in position within the sleeve 4. This allows a capsule portion of the capsule 10 to be received into the open end for connection with the capsule contact portion 18.

The capsule contact portion 18 has spring contacts (not shown) which are configured to provide electrical energy from the battery 12 to a heater element in the capsule 10 when the electronic cigarette 2 is in use. The plug portion 20 has electrical contacts (not shown) which allow the electronic cigarette 2 to be plugged into a charging port for the battery 12 to be recharged.

The sleeve 4 is made by extrusion of a metallic material through a die to form the tubular body. A hole (not shown) is drilled into the sleeve 4 to allow LED indication, such as device charging information, to be provided in the electronic cigarette 2.

The cross-section of the sleeves in the drawings is substantially oval-shaped with flat sides, but it should be understood that any shape could be used (for example rhombus-shaped, oval, circular, square or rectangular). The sleeve may also be made from other materials and processes, for example plastics, ceramics or a combination thereof and vacuum-forming, injection moulding or casting processes. A cast or moulded sleeve could be manufacture with one or both ends closed which may be subsequently machined to provide access to the inner space in the sleeve.

Figure 2A:
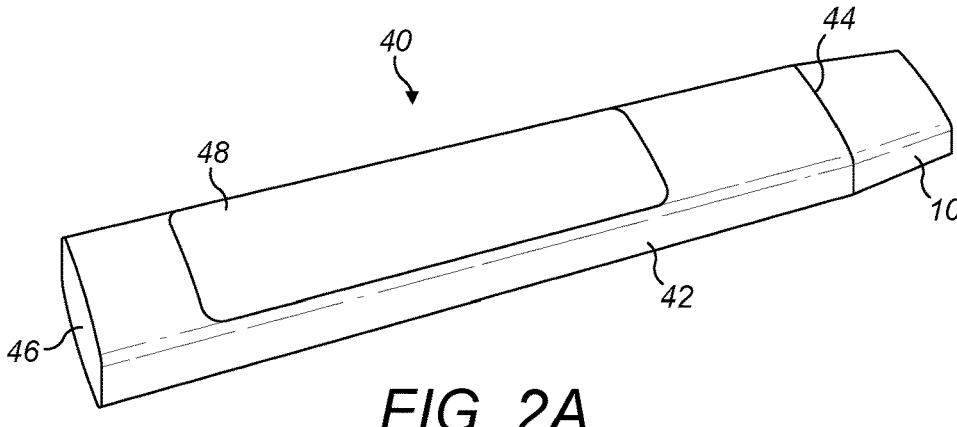
FIG. 2A is a perspective view of an assembled electronic cigarette in a first embodiment of the invention.
Figure 2B:
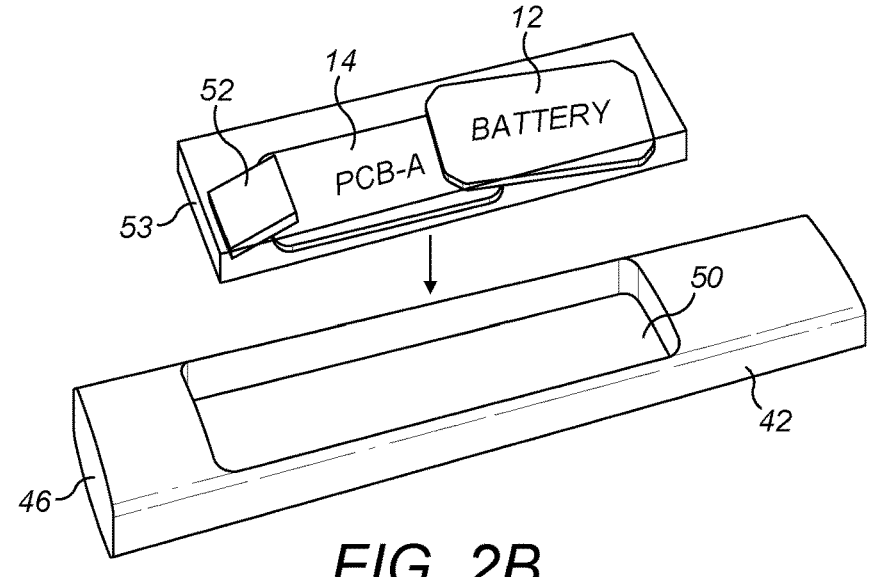
FIG. 2B is a perspective view of a pre-assembled electronic cigarette in the first embodiment of the invention.
Figure 2C:
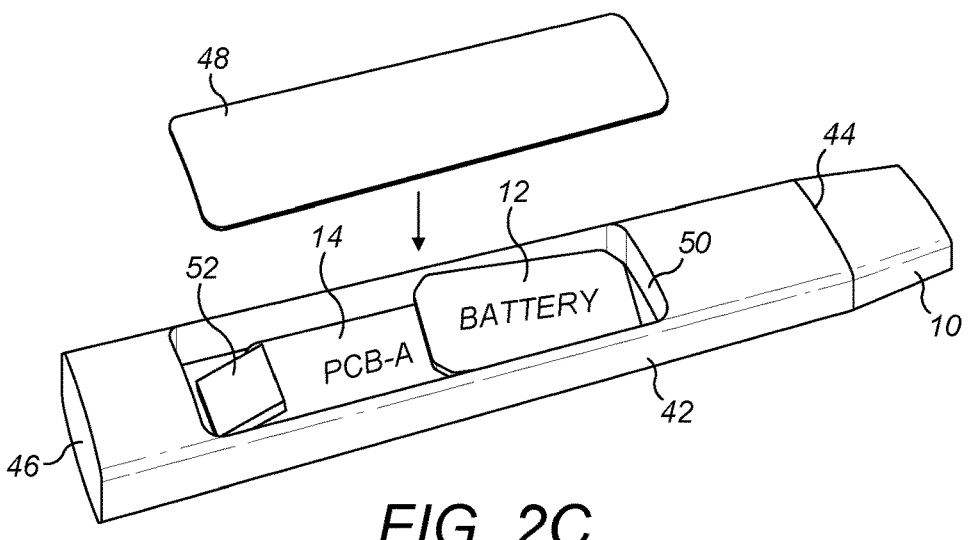
FIG. 2C is another perspective view of a pre-assembled electronic cigarette in the first embodiment of the invention.

FIG. 2A shows a perspective view of an assembled electronic cigarette 40 in an embodiment of the present invention. The electronic cigarette 40 has a sleeve 42 with a mouthpiece end 44 for receiving the capsule 10 and a charging end 46 for battery recharging purposes. The sleeve 42 has a lid 48 which covers a chamber section 50 as shown in FIGS. 2B and 2C. Similar to the electronic cigarette in the art (shown in FIG. 1) the sleeve 42 is preferably made as a single piece (e.g. by extrusion). The chamber section 50 comprises an opening configured to receive components.

The chamber section may be created by cutting a section out of the sleeve 42 to provide access to the inside of the sleeve 42 from its top side or a major surface of the sleeve 42. It is also possible to cast, injection-mould or vacuum-form a sleeve or housing with the chamber section provided, or alternatively a solid block of material can be machined into shape as required to provide the chamber section and holes for electrical and charging access and/or airflow.

FIG. 2B shows the sleeve 42 with the chamber section 50 in its top major surface to allow electronic components including a battery 12, PCB 14 and control circuitry 52 to be placed into the chamber section 50, as shown in FIG. 2C. The electronic components can be assembled on an insert (53) that is lowered into the chamber section 50 or alternatively each component can be individually placed into the sleeve 42. After the insert 53 and electronic components are placed into the sleeve 42 the lid 48 is placed over the opening of the chamber section 50.

The electronic cigarette 40 is configured to receive a pod 10, where the pod 10 contains an aerosol forming material and a heating element. However it should be understood that in an alternative configuration the heating element can be part of the electronic cigarette 40 and provided as an isolated component among the electronic components to be placed in the sleeve 42.

As shown in FIG. 2A, the lid 48 has a connection rim that is sized and shaped to match the circumferential edge of the opening. This has an advantage that the components housed in the sleeve 42 are sealed off and protected from external debris. The lid 48 may be attached onto the sleeve 42 in a friction fit connection. The friction fit connection can be achieved by using a push-fit mechanism with preferably a rubberised ring provided in the connection rim to seal the joint and provide shock-protection. Alternatively a magnetic connection can also be used. Optionally a groove (not shown) can be provided at the edge of the lid 48 and/or chamber section 50 for a tool to remove the lid 48 for repair or rework purposes. The lid 48 can also be configured as a door (e.g. a hinged connection) that allows a user to open in order to replace a battery or any other faulty electronic component.

Figure 3A:
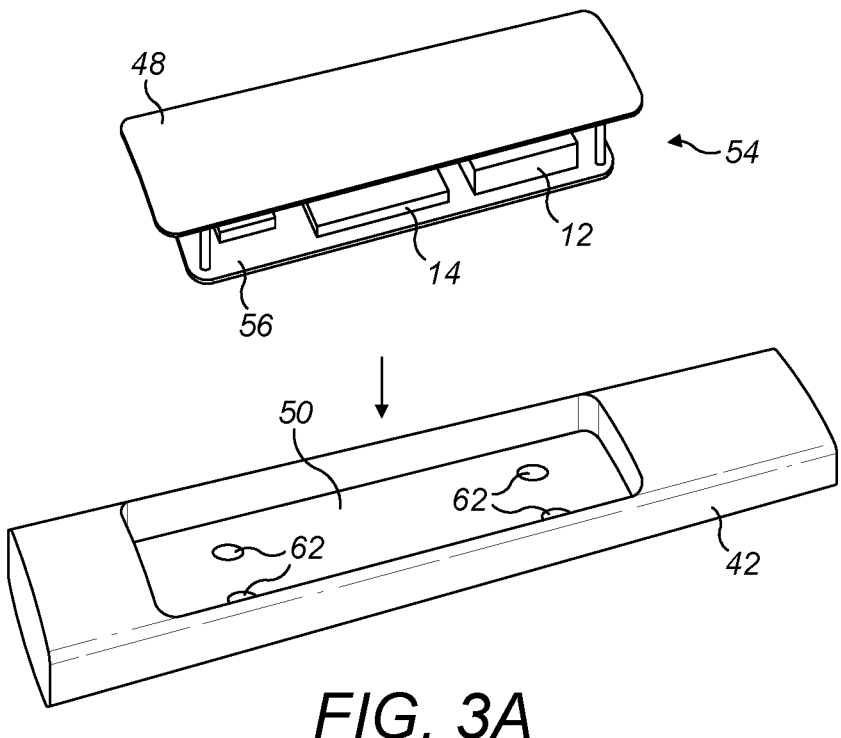
FIG. 3A is a perspective view of a pre-assembled electronic cigarette in a second embodiment of the invention.
Figure 3B:
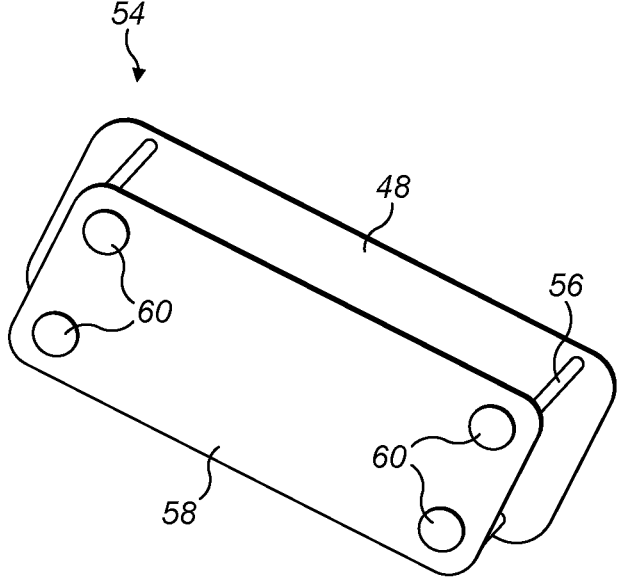
FIG. 3B is a perspective view from the base of an electronic module in the second embodiment of the invention.

FIG. 3A shows an alternative embodiment in which an electronic module 54 is provided as a single unit that is placed into the sleeve 42. The electronic module 54 comprises parts of or all electrical circuitry required to operate the electronic cigarette. The electronic module 54 has an outer frame structure, or chassis, 56 in which electrical components including the battery 12, PCB 14, control circuitry and any other electronic components are provided. FIG. 3B shows a perspective view of the electronic module 54 from the bottom of the module 54, where the electronic module 54 is shown to include a base plate 58 having a fastener 60 configured to guide or attach to corresponding contacts 62 in the chamber section 50 of the sleeve 42. In an embodiment, the fastener 60 may be in the form of magnetic contacts 60 and 62, which may optionally also act as electrical contacts for charging and heater power delivery purposes.

The lid 48 may advantageously be fixedly attached to the electronic module 54 prior to the electronic module 54 being inserted into the sleeve 42. This can be achieved using a friction fit (such as a push-fit) or screw fastening mechanism for example. By fixing the lid 48 to the electronic module 54 the entire modular unit can be easily removed from the electronic cigarette 40 for any repair works.

As an illustrative example FIGS. 4A, 4B, 4C and 4D show a lid 80 and display 82 in accordance with the present invention. It should be understood that the lid 80 can be manufactured separately from the sleeve of an electronic cigarette, which therefore allows the lid to be made from a different material, such as plastic (e.g. polymethyl methacrylate), glass, metal or a combination thereof. For example a laminated structure may be used in which a smaller glass layer is inset from and layered above or below a larger plastic layer. The outline or outer edge of the glass layer can have a rubber joint with mechanical clip features disposed around it, which acts as a seal and fastening mechanism to keep the glass and plastic layers in place and together.

The electronic cigarette may further comprise a display 82. The display 82 can be a separate component positioned over an opening in the body of the electronic cigarette 2. Hence, the display 82 of the present disclosure can be provided without the beforementioned advantageous manufacturing method including a top-mounted insert 53.

However, in a preferred embodiment, the digital display 82, such as an OLED display, liquid crystal, or electronic ink (e-ink) display for example, is integrated into the lid which is connected to the PCB or control electronics within the device. The display 82 can provide a user and/or device operational information such as puff count, duration of use, battery status and/or external information and notifications from a connected third party device, such as a calendar or other application in a smartphone.

Figure 4A:
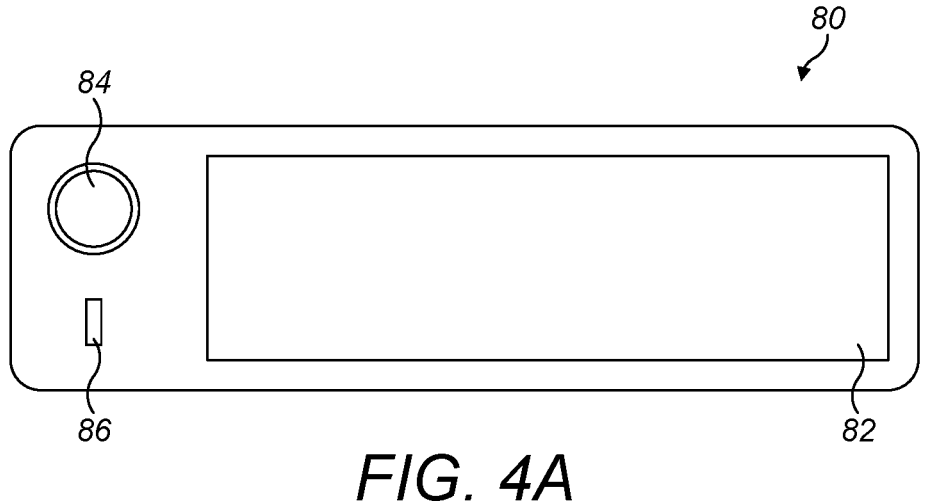
FIG. 4A is a top view of a lid in accordance with the invention.
Figure 4B:
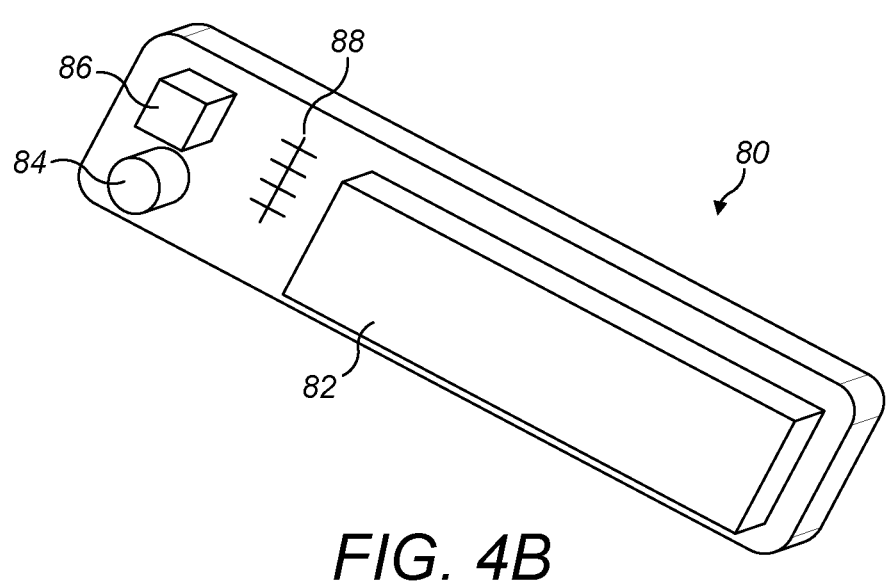
FIG. 4B is a perspective view from the base of the lid in accordance with the invention.
Figure 4C:
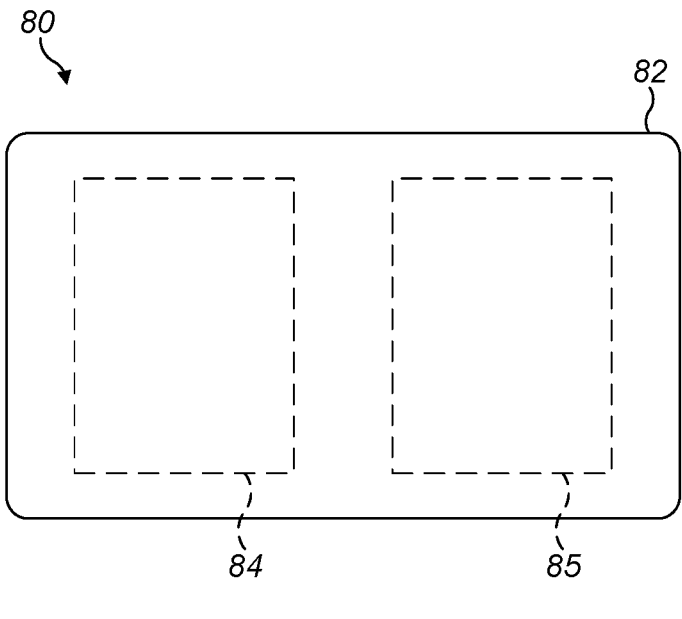
FIG. 4C is a top view of a lid in accordance with another embodiment of the invention.

Additional components can also be attached or integrated into the display 82 by using a plurality of different layers in the display 82 as shown in FIG. 4C, or alternatively the additional components can be set apart from the display 82 as depicted in FIGS. 4A and 4B. The additional components may include sensorial or biometric trackers 84 to detect one or more characteristics from a user (e.g. motion sensors, fingerprint sensors, heart-rate or blood oxygen monitors), airflow sensors 86, wireless antennas 88 for data or power communication, etc. The additional components may also include sensors that detect environmental conditions, such as temperature or humidity. In further example the additional components may be provided on the sleeve of the electronic cigarette.

A touch panel, which may be made of a thin glass sheet, can be placed on top of the display 82, where the touch panel can be silkscreened to hide the additional components below the display 82. It should therefore be understood that the display 82 can act as both an input device and an image display (i.e. similar to a touchscreen display in other electronic devices).

The display 82 can be made up of multiple layers, including one or more image display layers for providing information to a user and one or more transparent conductive layers for detecting user input, such as user touch commands or gestures, fingerprints, pulse, or other known biometrics. The conductive layers may include separate layers for authentication and sensing, where the authentication layer must provide a valid authentication to the control electronics before the sensing layer is activated. A user may provide authentication by inputting a PIN number, swipe pattern or other command to a touch panel. Alternatively authentication may be provided via fingerprint validation. A haptic indication may also be provided at the start or end of a user input recording to notify a user that an authentication or reading of biometric information (e.g. a fingerprint biometric heart signature) was successful.

Each of the layers in a biometric display may have substantially the same area, with each layer covering or superposed on a next layer. Alternatively the different conductive layers may have different sizes superposed to provide different zones for reading, authentication and sensing, where some zones may provide combined functions. For example a display may have a distinct zone for fingerprint authentication, and a separate zone for heart-rate monitoring, where the two zones are both provided under the display layer and general touch control layer.

Fingerprint authorization can also be integrated. This can be achieved by arranging a fingerprint scanner below the surface of the display. In order to enhance the readability, the display surface is advantageously configured with a geometry (curved radius) that ensures a sufficiently large contact zone between a user's finger and the display. The fingerprint recognition can also be used to read different commands as different fingers or portions of a single finger, like a "footprint", can be read. In other words different angles and combinations of fingers can be used in the fingerprint scanner to control different functions provided by the electronic device.

The properties of the material(s) of the lid should be selected in order for the functions of such additional components to be integrated or function through the lid; for example selecting a plastic lid that would allow preferential radio-frequency, RF, data transmission through the lid from an antenna in the device as compared to the RF transmissibility through the surrounding metal sleeve body, or configuring a portion of the lid to allow biometric scanning (e.g. heartbeat, fingerprint, etc.) to occur. FIG. 4B shows the underside of the lid 80 to which sensors and/or any other additional electronic components can be attached so that the body of a bulkier component can be stored in the chamber section of a device. This allows the top outer surface of the lid to be substantially flush with the outer surface of the sleeve when assembled.

Figure 4D:
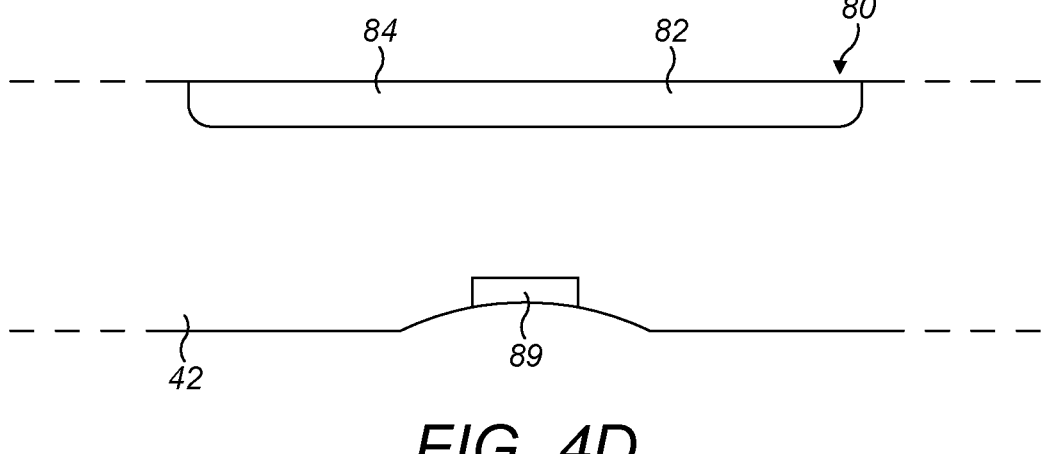
FIG. 4D is a schematic side view of an electronic cigarette in accordance with another embodiment of the invention.

FIG. 4D shows a schematic of another embodiment in which an additional sensor 89 is located in the sleeve 42 of the electronic cigarette, on a face of the sleeve opposite to the display 82. The additional sensor 89 may be a biometric sensor such as a heart-rate monitor or other biometric scanning device as described above. This additional sensor 89 is aligned with the sensor region, for example a fingerprint sensor 84, in the display 82 such that a user can easily place their finger or thumb on either sensor 82, 89. A weakening, for example a indented region, depression or notch, can also be provided around the additional sensor 89 to make the additional sensor 89 easier to locate.

In this embodiment it is possible for one sensor to be used as an activation or authentication sensor and the other sensor to function as a reading or data collection sensor. For example the sensor 84 in the display 82 may be a touch panel through which a user selects and activates a pulse or heart-rate monitoring function, whereby the user then places their thumb on the additional sensor 89 for the pulse to be read.

Different configurations for arranging components in the device and the lid would readily occur to a person skilled in the art. Importantly it should be understood that the lid allows an electronic cigarette to provide increased functionality to the user and protects the electronic components under the lid and in the sleeve.

Figure 5A:
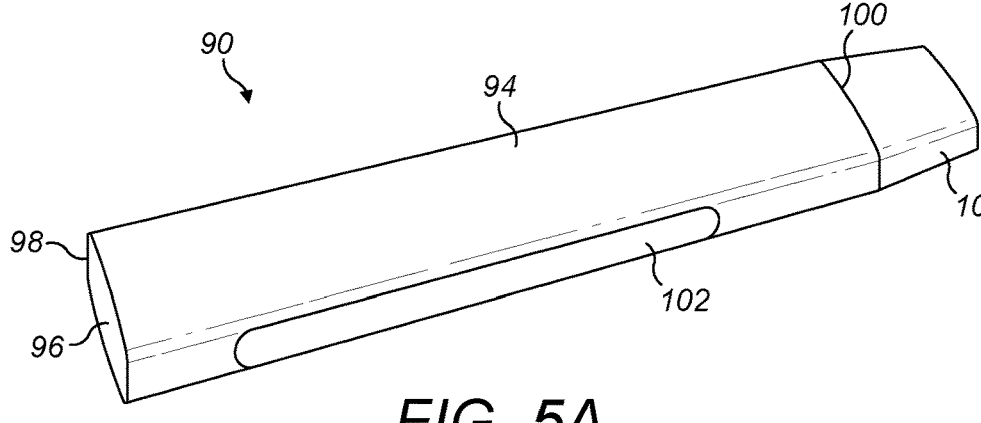
FIG. 5A is a perspective view of an assembled electronic cigarette in a third embodiment of the invention.
Figure 5B:
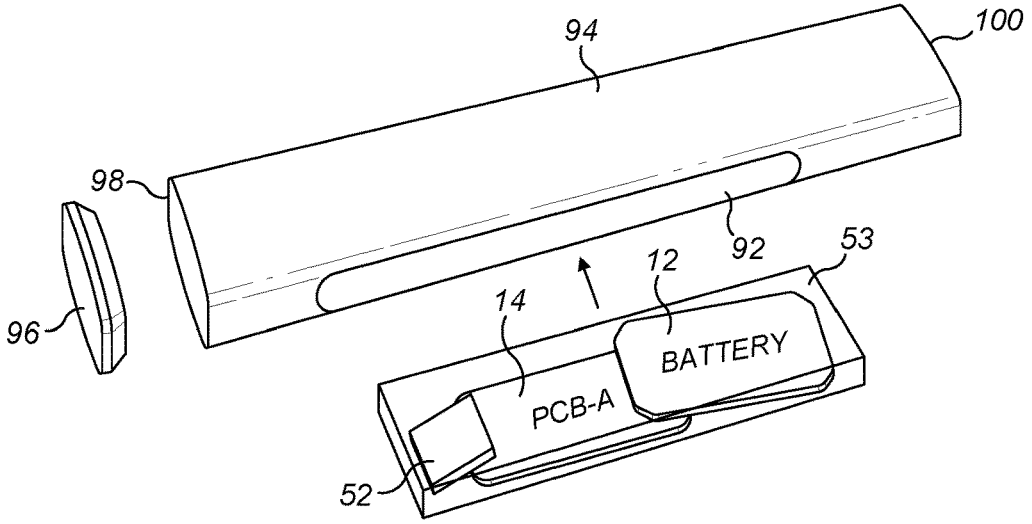
FIG. 5B is a perspective view of a pre-assembled electronic cigarette in the third embodiment of the invention.
Figure 5C:
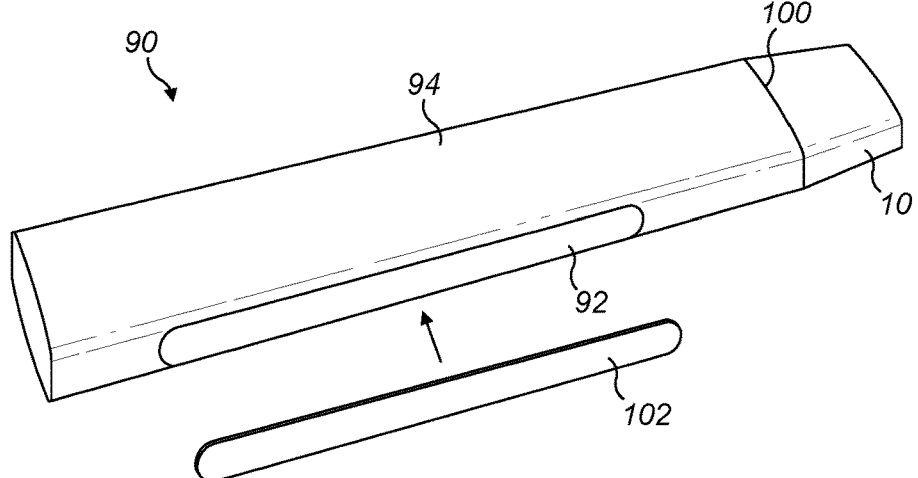
FIG. 5C is another perspective view of a pre-assembled electronic cigarette in the third embodiment of the invention.

FIG. 5 shows an electronic cigarette 90 in another embodiment of the invention. In this arrangement the electronic components are inserted into the electronic cigarette 90 from a side entry chamber 92 in the sleeve 94. The side entry chamber 92 may be created in a similar way as the previously described top entry chamber 50. Hence, the side entry chamber 92 can be created by cutting a section out of the sleeve 94 in a similar way to the top entry embodiment of the invention. A plug 96 is preferably inserted at a charging end 98 of the device 90, and a pod 10 is inserted at a mouthpiece end 100 of the device 90. The plug 96 can be made of a RF transmissive material and/or include access ports (not shown) for electrical or data communication access. The access ports may also include embedded magnets for connection to other devices such as a docking or charging hub, or other electronic add-ons that may enhance the device (e.g. additional display or light feature, power bank or external storage).

The electronic components can be assembled on a tray 53, or insert, that slides into the chamber section 92, after which a lid 102 is placed over the side opening of the chamber section 92. Alternatively, similar to the embodiment described above corresponding to FIGS. 3A and 3B, the electronic components are assembled in a frame structure (not shown) with the lid 102 fixedly attached, where the electronic components and the frame are provided as a single electronic module that is inserted into the sleeve 94.

The invention claimed is:

1. An electronic cigarette, comprising:
an external housing having a notch or depression and a surface, the surface extending into the notch or depression;
a display unit having a first biometric sensor, the display unit located in an aperture of the external housing and configured to receive user input and display operational status of the electronic cigarette, wherein:
the first biometric sensor is configured to detect a first characteristic from the user input, and
the aperture in which the display unit is located is opposite the notch or depression; and
a second biometric sensor configured to detect a second characteristic from the user, wherein:
the second biometric sensor is located within the notch or depression, the second biometric sensor is activated based on the activation of the first biometric sensor, and
the second characteristic is different from the first characteristic.

2. The electronic cigarette according to claim 1, wherein a display of the display unit comprises a plurality of layers, where a first layer of the plurality of layers is configured to sense an input from the user and activate the first biometric sensor.

3. The electronic cigarette according to claim 2, wherein a second layer of the plurality of layers is an input area of the first biometric sensor.

4. The electronic cigarette according to claim 3, wherein the second layer is activated based on activation of the first layer.

5. The electronic cigarette according to claim 3, wherein the first layer and the second layer are superposed.

6. The electronic cigarette according to claim 3, wherein the second layer is a pixeled layer and wherein the first layer defines a reading zone of the pixeled second layer.

7. The electronic cigarette according to claim 1, wherein the first biometric sensor is configured to detect a movement or position in space of the electronic cigarette.

8. The electronic cigarette according to claim 1, wherein the first biometric sensor is an optical sensor.

9. The electronic cigarette according to claim 1, wherein the first biometric sensor is a fingerprint reader.

10. The electronic cigarette according to claim 1, wherein the first biometric sensor is a heart rate sensor.

11. The electronic cigarette according to claim 1, wherein the external housing comprises an electrically conductive material and is connected to a circuit configured to register a heartbeat of a user.

12. The electronic cigarette according to claim 1, further comprising a controller configured to retrieve information from the first biometric sensor and control operation of the electronic cigarette.

13. The electronic cigarette according to claim 1, wherein the display unit is provided as an exterior surface comprising at least one electronic component.

14. The electronic cigarette according to claim 13, wherein the exterior surface is a top surface on an insert of the electronic cigarette.

15. An electronic cigarette, comprising:
a housing sleeve having a notch or depression;
a sensor configured to detect a first characteristic from a user;
a display unit having a first biometric sensor, the display unit located in an aperture of the housing sleeve and configured to receive user input and display operational status of the electronic cigarette, wherein:
the first biometric sensor is configured to detect a first characteristic from the user input, and
the aperture in which the display unit is located is opposite the notch or depression; and
a second biometric sensor located in the housing sleeve, wherein:
the second biometric sensor is located within the notch or depression, the second biometric sensor is activated based on the activation of the first biometric sensor, and
the second biometric sensor is configured to detect a second characteristic different from the first characteristic.

* * * * *